(12) United States Patent
Rodes Solanes et al.

(10) Patent No.: US 10,106,522 B2
(45) Date of Patent: Oct. 23, 2018

(54) BENZIMIDAZOLE DERIVATIVES AS ANTIHISTAMINE AGENTS

(71) Applicant: Faes Farma, S.A., Leioa-Vizcaya (ES)

(72) Inventors: Rosa Rodes Solanes, Leioa-Vizcaya (ES); Roberto Olivera Tizne, Leioa-Vizcaya (ES); Gonzalo Hernández Herrero, Leioa-Vizcaya (ES); Víctor Rubio Royo, Leioa-Vizcaya (ES); Francisco Ledo Gómez, Leioa-Vizcaya (ES)

(73) Assignee: Faes Farma, S.A., Leioa-Vizcaya (ES)

( * ) Notice: Subject to any disclaimer, the term of this patent is extended or adjusted under 35 U.S.C. 154(b) by 0 days.

(21) Appl. No.: 15/540,905

(22) PCT Filed: Dec. 28, 2015

(86) PCT No.: PCT/EP2015/081292
§ 371 (c)(1),
(2) Date: Jun. 29, 2017

(87) PCT Pub. No.: WO2016/107848
PCT Pub. Date: Jul. 7, 2016

(65) Prior Publication Data
US 2018/0016251 A1 Jan. 18, 2018

(30) Foreign Application Priority Data
Dec. 29, 2014 (EP) .................................. 14382576

(51) Int. Cl.
*C07D 401/04* (2006.01)
*C07D 401/14* (2006.01)
*C07D 471/04* (2006.01)

(52) U.S. Cl.
CPC ......... *C07D 401/04* (2013.01); *C07D 401/14* (2013.01); *C07D 471/04* (2013.01)

(58) Field of Classification Search
CPC ... C07D 401/04; C07D 471/04; C07D 401/14
See application file for complete search history.

(56) References Cited

FOREIGN PATENT DOCUMENTS

| | | | |
|---|---|---|---|
| CN | 103896915 | * | 7/2014 |
| EP | 0580541 | | 1/1994 |
| EP | 0818454 | | 1/1998 |
| JP | 2001011050 | * | 1/2001 |
| JP | 2002322059 | * | 11/2002 |
| WO | WO-1992001697 | | 2/1992 |
| WO | WO-2000075130 | | 12/2000 |
| WO | 2002034719 | * | 5/2002 |
| WO | 2002036122 | * | 5/2002 |
| WO | WO-2016107848 | | 7/2016 |

OTHER PUBLICATIONS

Jiudaka, Kei, et al., "Simple method for quantitation of enhanced vascular permeability", Proc. Soc. Exp. Biol. Med. 1970;133:1384-1387, (1970), 1384-1387.
Lefebvre, P., et al., "Influence of ε-aminocaproic acid on the increase in vascular permeability induced by histamine in rats", C. R. Soc. Biol. 156, 183-186 (1962), (1962), 183-186.
Mota, Ivan, "Passive Cutaneous Anaphylaxis Induced With Mast Cell-Sensitizing Antibody. The Role of Histamine and 5-Hydroxytryptamine", Life Sciences, vol. 2, Issue 12, Dec. 1963, pp. 917-927, (Dec. 1963), 917-927.
"International Application No. PCT/EP2015/081292, International Search Report and Written Opinion dated Mar. 21, 2016", (Mar. 21, 2016), 10 pgs.

* cited by examiner

*Primary Examiner* — D Margaret M Seaman
(74) *Attorney, Agent, or Firm* — Schwegman Lundberg & Woessner, P.A.

(57) ABSTRACT

The invention relates to compounds of formula (I), or a pharmaceutically acceptable salt or solvate thereof, a method of synthesis of said compounds, pharmaceutical compositions comprising them and their use in the treatment and/or prevention of conditions mediated by $H_1$ histamine receptor, such as allergic disorders or diseases.

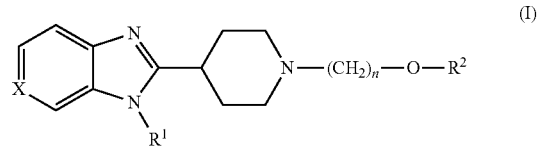

9 Claims, No Drawings

BENZIMIDAZOLE DERIVATIVES AS ANTIHISTAMINE AGENTS

PRIORITY CLAIM TO RELATED APPLICATIONS

This application is a U.S. national stage application filed under 35 U.S.C. § 371 from International Application Serial No. PCT/EP2015/081292, which was filed 28 Dec. 2015, and published as WO2016/107848 on 7 Jul. 2016, and which claims priority to European Application No. 14382576.8, filed 29 Dec. 2014, which applications and publication are incorporated by reference as if reproduced herein and made a part hereof in their entirety, and the benefit of priority of each of which is claimed herein.

FIELD OF THE INVENTION

The present invention relates to new benzimidazole derivatives, method of synthesis, pharmaceutical compositions comprising them and their use as antihistamine and antiallergic agents.

STATE OF THE ART

It has long been known that histamine plays a very important role in allergic-type diseases, such as allergic rhinitis, conjunctivitis, rhinoconjunctivitis, dermatitis, urticaria and asthma. Antihistaminic compounds acting at the histamine $H_1$-receptor level are useful for treating such conditions.

First generation $H_1$ antihistamines presented a number of adverse effects resulting from its action on the central nervous system and cholinergic receptors.

The search for molecules that would not cross the blood-brain barrier brought about the displacement of the early antihistamines by other second generation antihistamines which overcame the side effects linked to their action on the central nervous system. This new generation of antihistamines has recently displayed a negative aspect in the form of dangerous cardiovascular effects, extending the QT space and ventricular arrhythmia, which has required its use to be avoided in those cases in which the patient is prone to suffering such disturbances or when he is being treated with substances that may interfere with his metabolism.

Attempts at obtaining safe and efficient $H_1$ antihistamines have multiplied in recent years and this research has resulted in several recent patent applications claiming pharmaceutical compositions for treating allergic diseases containing antihistamines devoid of arrhythmogenic effects.

Documents EP 0818454 A1 and EP 0580541 A1 disclose benzimidazole compounds with selective $H_1$ antihistaminic activity.

However, there still remains a need to find new and alternative compounds to treat allergic diseases or disorders for complementing the already existing choice of active ingredients. The present invention relates to a group of new compounds with benzimidazolic structure having potent selective $H_1$ antihistaminic activity, lacking activity on the central nervous system and on the cardiovascular system.

SUMMARY OF THE INVENTION

The authors of the present invention have found that compounds of formula (I) show activity as histamine $H_1$-receptor antagonists and are therefore useful in the treatment of allergic disorders or diseases.

Therefore, according to a first aspect, the present invention is directed to a compound of formula (I):

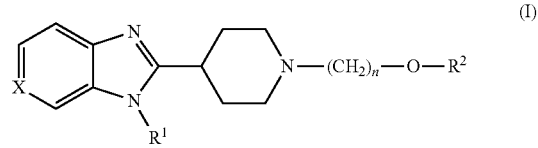

wherein:
$R^1$ is an optionally substituted $C_1$-$C_6$ alkyl group;
$R^2$ is selected from hydrogen, —$COR_b$, —$COOR_c$, optionally substituted $C_1$-$C_6$ alkyl, optionally substituted $C_3$-$C_7$ cycloalkyl and optionally substituted 3- to 10-membered heterocyclyl, wherein $R_b$ and $R_c$ are independently selected from $C_1$-$C_6$ alkyl, halo($C_1$-$C_6$ alkyl), $C_3$-$C_7$ cycloalkyl, 3- to 10-membered heterocyclyl, $C_6$-$C_{12}$ aryl, ($C_6$-$C_{12}$)aryl($C_1$-$C_6$)alkyl, and 3- to 10-membered heteroaryl;
n is 1, 2 or 3;
X is CH or N;
or a pharmaceutically acceptable salt or solvate thereof.

According to a further aspect, the present invention is directed to a pharmaceutical composition comprising a compound of formula (I) as defined above, or a pharmaceutically acceptable salt or solvate thereof, and at least one pharmaceutically acceptable excipient.

A further aspect of the invention refers to a compound of formula (I) as defined above, or a pharmaceutically acceptable salt or solvate thereof, for use as a medicament.

A further aspect of the invention are the compounds of formula (I) as defined above, or a pharmaceutically acceptable salt or solvate thereof, for use in the treatment and/or prevention of a disorder or disease susceptible to amelioration by antagonism of $H_1$ histamine receptor.

A further aspect of the invention are the compounds of formula (I) as defined above, or a pharmaceutically acceptable salt or solvate thereof, for use in the treatment and/or prevention of an allergic disorder or disease.

According to a further aspect, the present invention is directed to the use of a compound of formula (I) as defined above, or a pharmaceutically acceptable salt or solvate thereof, in the preparation of a medicament for the treatment and/or prevention of a disorder or disease susceptible to amelioration by antagonism of $H_1$ histamine receptor.

According to a further aspect, the present invention is directed to the use of a compound of formula (I) as defined above, or a pharmaceutically acceptable salt or solvate thereof, in the preparation of a medicament for the treatment and/or prevention of an allergic disorder or disease.

In a further aspect, the invention is directed to a method of treating and/or preventing a disorder or disease susceptible to amelioration by antagonism of $H_1$ histamine receptor, said method comprising administering to a patient in need of such a treatment and/or prevention a therapeutically effective amount of at least one compound of formula (I) as described above, or a pharmaceutically acceptable salt or solvate thereof.

In a further aspect, the invention is directed to a method of treating and/or preventing an allergic disorder or disease, said method comprising administering to a patient in need of such a treatment and/or prevention a therapeutically effective amount of at least one compound of formula (I) as described above, or a pharmaceutically acceptable salt or solvate thereof.

DETAILED DESCRIPTION OF THE INVENTION

In the context of the present invention, the following terms have the meaning detailed below:

The term "$C_{1-6}$ alkyl" refers to a linear or branched hydrocarbon chain radical consisting of carbon and hydrogen atoms, containing no insaturation, having between 1 and 6, preferably between 1 and 3 ("$C_{1-3}$ alkyl"), carbon atoms and which is attached to the rest of the molecule by a single bond, including for example and in a non-limiting sense, methyl, ethyl, n-propyl, i-propyl, n-butyl, t-butyl, n-pentyl, etc. Preferably "alkyl" refers to methyl or ethyl.

The term "$C_{3-7}$ cycloalkyl" refers to a saturated or partially saturated mono- or bicyclic aliphatic group having between 3 and 7, preferably between 3 and 6 carbon atoms which is bound to the rest of the molecule by means of a single bond, including for example and in a non-limiting sense, cyclopropyl, cyclohexyl, cyclopentyl, etc.

The term "$C_{6-12}$ aryl" refers to an aromatic group having between 6 and 12, preferably between 6 and 10 ("$C_{6-10}$ aryl"), more preferably 6 or 10 carbon atoms, comprising 1 or 2 aromatic nuclei, bound by means of a carbon-carbon bond or fused, including for example and in a non-limiting sense, phenyl, naphthyl, diphenyl, etc. Preferably "aryl" refers to phenyl.

"3- to 10-membered heterocyclyl" refers to a stable 3- to 10-membered ring radical, preferably a 5- or 6-membered ring, which consists of carbon atoms and from one to five heteroatoms selected from the group consisting of nitrogen, oxygen, and sulphur and which can be partially or fully saturated. For the purposes of this invention, the heterocycle can be a monocyclyl or bicyclyl ring system. Examples of such heterocycles include, but are not limited to, pyrrolidine, piperidine, piperazine, morpholine, tetrahydrofuran.

"3- to 10-membered heteroaryl" refers to a stable 3- to 10-membered aromatic ring radical, preferably a 5- or 6-membered aromatic ring, which consists of carbon atoms and from one to five heteroatoms selected from the group consisting of nitrogen, oxygen, and sulphur. For the purposes of this invention, the heteroaryl can be a monocyclyl or bicyclyl ring system, which can include systems of fused rings. Examples of such heteroaryl include, but are not limited to, benzimidazole, benzothiazole, benzofuran, furan, pyrrole, thiazole, pyrazole, pyridine, pyrimidine, isothiazole, imidazole, indole, purine, quinoline, thiadiazole. Preferably "heteroaryl" refers to pyridine.

The term "$(C_6-C_{12})aryl(C_1-C_6)alkyl$" refers to an aryl group as defined above which is attached to the rest of the molecule through an alkyl group as defined above.

The term "$halo(C_1-C_6\ alkyl)$" refers to an alkyl group as defined above wherein at least one of the hydrogen atoms has been replaced by a halogen atom such as, for example $CF_3$, $CCl_3$, $CHF_2$, $CF_2CF_3$, etc. Preferably "$halo(C_1-C_6\ alkyl)$" refers to $CF_3$.

The term "halogen" or "halo" or "Hal" refers to bromo, chloro, iodo or fluoro.

As understood in this technical area, there can be a certain degree of substitution on the previously defined radicals. Thus, there can be substitution in any of the groups of the present invention. The references of the present document to substituted groups in the groups of the present invention indicate that the specified radical can be substituted in one or more available positions by one or more substituents. Said substituents include, for example and in a non-limiting sense, $C_{1-6}$ alkyl, $halo(C_1-C_6\ alkyl)$, cycloalkyl, $C_3-C_7$ cycloalkyl, 3- to 10-membered heterocyclyl, $C_6-C_{12}$ aryl, $(C_6-C_{12})aryl(C_1-C_6)alkyl$, or 3- to 10-membered heteroaryl, halogen, CN, $NO_2$, —$OR_d$, —$COR_e$, —$COOR_f$, —$CONR_gR_h$, —$OCOR_i$, —$SR_j$, —$NR_kR_l$; wherein each $R_d$, $R_e$, $R_f$, $R_g$, $R_h$, $R_i$, $R_j$, $R_k$ and $R_l$ are independently selected from hydrogen, $C_1-C_6$ alkyl, $halo(C_1-C_6\ alkyl)$, $C_6-C_{12}$ aryl, $(C_6-C_{12})aryl(C_1-C_6)alkyl$, 3- to 10-membered heterocyclyl, and 3- to 10-membered heteroaryl.

Compounds of Formula (I)

An embodiment of the invention is directed to a compound of formula (I):

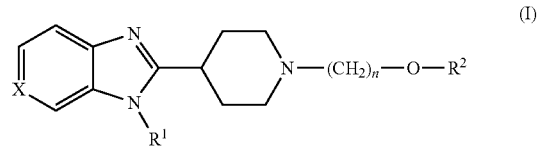

(I)

as previously defined, or a pharmaceutically acceptable salt or solvate thereof.

According to a particular embodiment, n is 1 or 2. According to another particular embodiment, n is 2 or 3. Preferably, n is 2.

According to a particular embodiment, $R^1$ is a $C_1-C_6$ alkyl group optionally substituted with $C_1-C_6$ alkyl, $C_3-C_7$ cycloalkyl, 3- to 10-membered heterocyclyl, $C_6-C_{12}$ aryl, 3- to 10-membered heteroaryl, halogen, CN, $NO_2$, $NH_2$, $NH(C_1-C_6\ alkyl)$, $N(C_1-C_6\ alkyl)_2$, or —$OR_a$, wherein $R_a$ is selected from hydrogen, $C_1-C_6$ alkyl, $halo(C_1-C_6\ alkyl)$, $C_3-C_7$ cycloalkyl, 3- to 10-membered heterocyclyl, $C_6-C_{12}$ aryl, $(C_6-C_{12})aryl(C_1-C_6)alkyl$, and 3- to 10-membered heteroaryl.

Preferably, $R^1$ is a $C_1-C_6$ alkyl group optionally substituted with $C_6-C_{12}$ aryl, 3- to 10-membered heteroaryl, or —$OR_a$, wherein $R_a$ is selected from hydrogen, $C_1-C_6$ alkyl, $C_6-C_{12}$ aryl, $(C_6-C_{12})aryl(C_1-C_6)alkyl$, and 3- to 10-membered heteroaryl. More preferably, $R^1$ is a $C_1-C_6$ alkyl group optionally substituted with $C_6-C_{12}$ aryl, 5- to 6-membered heteroaryl or —$OR_a$, wherein $R_a$ is selected from hydrogen, $C_1-C_6$ alkyl, $C_6-C_{12}$ aryl, $(C_6-C_{12})aryl(C_1-C_6)alkyl$, and 3- to 10-membered heteroaryl. Even more preferably, $R^1$ is a $C_1-C_6$ alkyl group optionally substituted with —$OR_a$, wherein $R_a$ is selected from hydrogen, $C_1-C_6$ alkyl, $C_6-C_{12}$ aryl, $(C_6-C_{12})aryl(C_1-C_6)alkyl$, and 3- to 10-membered heteroaryl. Even more preferably, $R^1$ is a $C_1-C_6$ alkyl group optionally substituted with 5- to 6-membered heteroaryl (such as pyridinyl) or —$OR_a$, wherein $R_a$ is selected from $C_1-C_6$ alkyl, phenyl, and 5- to 6-membered heteroaryl. Still more preferably, $R^1$ is a $C_1-C_6$ alkyl group optionally substituted with —$OR_a$, wherein $R_a$ is selected from $C_1-C_6$ alkyl, phenyl, and 5- to 6-membered heteroaryl.

According to another preferred embodiment, $R^1$ is a $C_1-C_6$ alkyl group optionally substituted with —$OC_{1-6}$ alkyl. Preferably, $R^1$ is a $C_1-C_3$ alkyl group optionally substituted with —$OC_{1-3}$ alkyl. In a particular embodiment, $R^1$ is —$CH_2CH_2OCH_2CH_3$.

According to a particular embodiment, $R^2$ is selected from hydrogen; —$COR_b$; —$COOR_c$; $C_1-C_6$ alkyl optionally substituted with —$OR_d$, —$COR_e$, —$COOR_f$, —$CONR_gR_h$, —$OCOR_i$, —$SR_j$, —$NR_kR_l$, halogen, CN, $NO_2$, $C_1-C_6$ alkyl, $C_3-C_7$ cycloalkyl, 3- to 10-membered heterocyclyl, $C_6-C_{12}$ aryl, $(C_6-C_{12})aryl(C_1-C_6)alkyl$, or 3- to 10-membered heteroaryl; $C_3-C_7$ cycloalkyl optionally substituted with —$OR_d$, —$COR_e$, —$COOR_f$, —$CONR_gR_h$, —$OCOR_i$, —$SR_j$, —$NR_kR_l$, halogen, CN, $NO_2$, $C_1-C_6$ alkyl, $C_3-C_7$ cycloalkyl, 3- to 10-membered heterocyclyl, $C_6-C_{12}$ aryl, ($C_6$-$C_{12}$)aryl($C_1$-$C_6$)alkyl, or 3- to 10-membered heteroaryl; and $C_3$-$C_7$ cycloalkyl optionally substituted with —$OR_d$, —$COR_e$, —$COOR_f$, —$CONR_gR_h$, —$OCOR_i$, —$SR_j$, —$NR_kR_l$, halogen, CN, $NO_2$, $C_1$-$C_6$ alkyl, $C_3$-$C_7$ cycloalkyl, 3- to 10-membered heterocyclyl, $C_6$-$C_{12}$ aryl, ($C_6$-$C_{12}$)aryl($C_1$-$C_6$)alkyl, or 3- to 10-membered heteroaryl; wherein each $R_b$, $R_c$, $R_d$, $R_e$, $R_f$, $R_g$, $R_h$, $R_i$, $R_j$, $R_k$ and $R_l$ are independently selected from hydrogen, $C_1$-$C_6$ alkyl, halo ($C_1$-$C_6$ alkyl), $C_6$-$C_{12}$ aryl, ($C_6$-$C_{12}$)aryl($C_1$-$C_6$)alkyl, and 3- to 10-membered heteroaryl.

Preferably, $R^2$ is selected from hydrogen, —$COR_b$, —$COOR_c$ and $C_1$-$C_6$ alkyl optionally substituted with —$OR_d$, —$COR_e$, —$COOR_f$, —$CONR_gR_h$, —$OCOR_i$, —$SR_j$, —$NR_kR_l$, halogen, CN, $NO_2$, $C_1$-$C_6$ alkyl, $C_3$-$C_7$ cycloalkyl, 3- to 10-membered heterocyclyl, $C_6$-$C_{12}$ aryl, ($C_6$-$C_{12}$)aryl($C_1$-$C_6$)alkyl, or 3- to 10-membered heteroaryl; wherein each $R_b$, $R_c$, $R_d$, $R_e$, $R_f$, $R_g$, $R_h$, $R_i$, $R_j$, $R_k$ and $R_l$ are independently selected from hydrogen, $C_1$-$C_6$ alkyl, halo ($C_1$-$C_6$ alkyl), $C_6$-$C_{12}$ aryl, ($C_6$-$C_{12}$)aryl($C_1$-$C_6$)alkyl, and 3- to 10-membered heteroaryl. More preferably, $R^2$ is selected from hydrogen, —$COR_b$, —$COOR_c$ and $C_1$-$C_6$ alkyl optionally substituted with —$OR_d$, or —$COOR_e$, wherein $R_b$, $R_c$, $R_d$ and $R_e$ are independently selected from hydrogen and $C_1$-$C_6$ alkyl. Even more preferably, $R^2$ is selected from hydrogen, —$COR_b$, and $C_1$-$C_6$ alkyl optionally substituted with —$OR_d$, or —$COOR_e$, wherein $R_b$, $R_d$ and $R_e$ are independently selected from hydrogen and $C_1$-$C_6$ alkyl.

According to another preferred embodiment, $R^2$ is selected from hydrogen, —$COR_b$ and $C_1$-$C_3$ alkyl optionally substituted with —$OC_{1-3}$ alkyl, —COOH or —$COOC_{1-3}$ alkyl. In a particular embodiment, $R^2$ is selected from hydrogen, $COCH_3$, —$CH_2COOH$, —$CH_2COOCH_3$, $CH_2COOCH_2CH_3$ and —$CH_2CH_2OCH_2CH_3$.

According to a preferred embodiment, X is CH. In an alternative embodiment X is N.

According to another embodiment of the present invention, the compounds of formula (I) are preferably selected from the group consisting of:

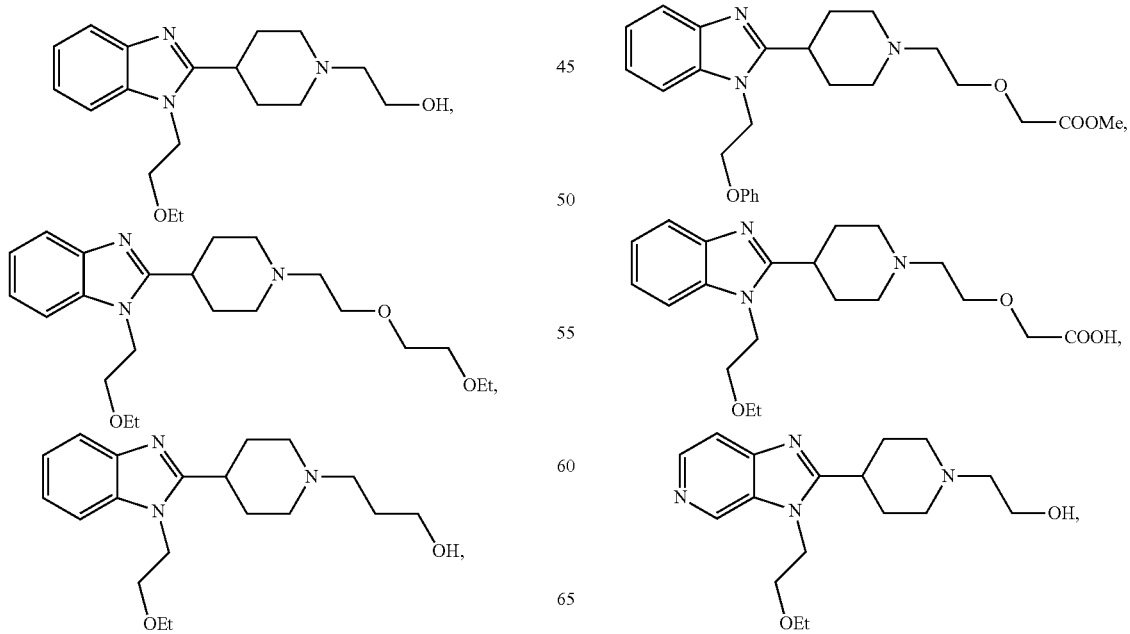

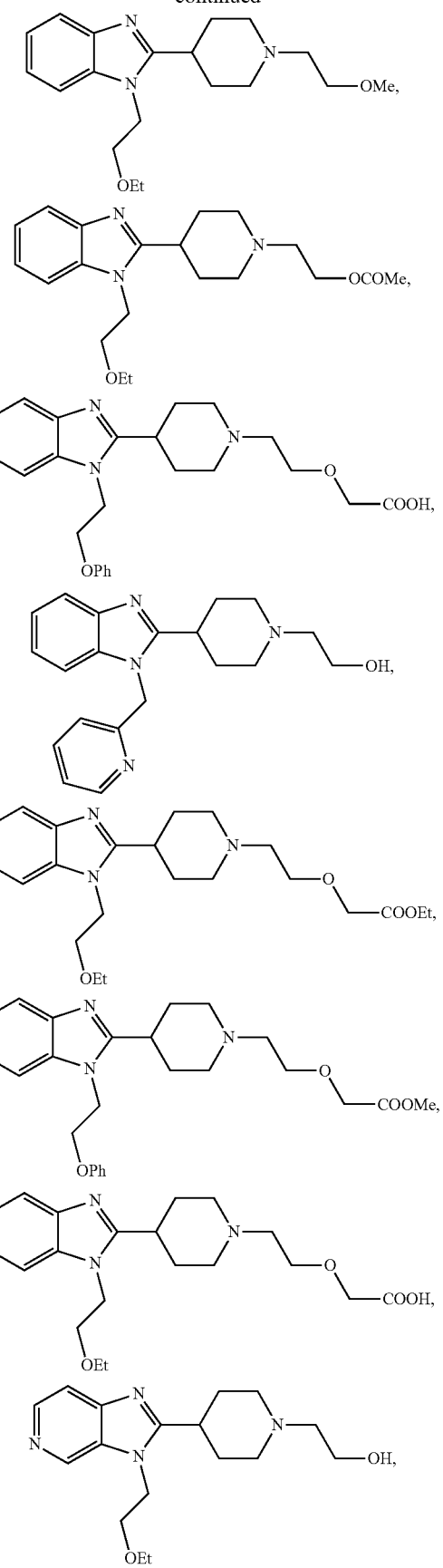

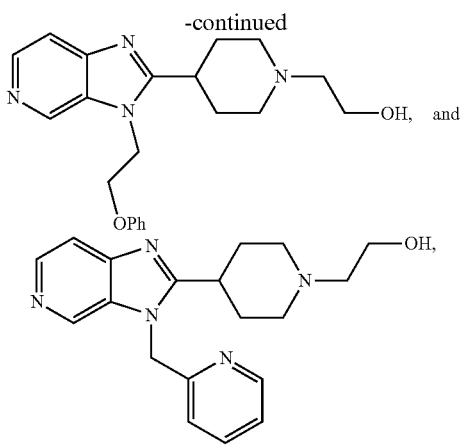

or a pharmaceutically acceptable salt or solvate thereof.

The compounds of formula (I) may be in the form of salts or solvates, preferably pharmaceutically acceptable salts or solvates.

The invention also provides "salts" of the compounds described herein. By way of illustration, said salts can be acid addition salts, base addition salts or metal salts, and can be synthesized from the parent compounds containing a basic or acid moiety by means of conventional chemical processes known by the persons skilled in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts.

The term "solvate" according to this invention is to be understood as meaning any form of the active compound according to the invention which has another molecule (most likely a polar solvent) attached to it via non-covalent bonding. Examples of solvates include hydrates and alcoholates. Solvation methods are generally known in the state of the art.

The term "pharmaceutically acceptable" relates to molecular entities and compositions being physiologically tolerable and normally not causing an allergic reaction or similar adverse reaction, such as gastric discomfort, dizziness and the like, when they are administered to a human being. Preferably, as used in this description, the term "pharmaceutically acceptable" means approved by a governmental regulatory agency or listed in the US pharmacopoeia or another generally recognized pharmacopoeia for use in animals, and more particularly in humans.

One preferred pharmaceutically acceptable form is the crystalline form. The compounds of the invention may present different polymorphic forms, it is intended that the invention encompasses all such forms.

The compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon or a nitrogen by $^{15}N$-enriched nitrogen are within the scope of this invention.

Uses of Compounds of Formula (I)

Compounds of formula (I) have been found to be antagonists of histamine $H_1$ receptor and would thus be useful in the treatment and/or prevention of diseases known to be susceptible to improvement by antagonism of histamine $H_1$ receptor.

Therefore, an aspect of the invention refers to a compound of formula (I) as defined above, or a pharmaceutically acceptable salt or solvate thereof, for use as a medicament.

In another aspect, the invention is directed to a compound of formula (I) as defined above, or a pharmaceutically acceptable salt or solvate thereof, for use in the treatment and/or prevention of a disorder or disease susceptible to amelioration by antagonism of $H_1$ histamine receptor. Such diseases are, for example, allergic diseases or disorders.

Therefore, in another aspect, the invention is directed to a compound of formula (I) as defined above, or a pharmaceutically acceptable salt or solvate thereof, for use in the treatment and/or prevention of an allergic disease or disorder. Preferably, an allergic disease or disorder selected from rhinitis, conjunctivitis, rhinoconjunctivitis, dermatitis, urticaria and asthma.

The term "treatment" or "to treat" in the context of this specification means administration of a compound or formulation according to the invention to ameliorate or eliminate the disease or one or more symptoms associated with said disease. "Treatment" also encompasses ameliorating or eliminating the physiological sequelae of the disease.

The term "ameliorate" in the context of this invention is understood as meaning any improvement on the situation of the patient treated.

The term "prevention" or "to prevent" in the context of this specification means administration of a compound or formulation according to the invention to reduce the risk of acquiring or developing the disease or one or more symptoms associated with said disease.

Pharmaceutical Compositions

According to a further aspect, the present invention is directed to a pharmaceutical composition comprising a compound of formula (I) as defined above, or a pharmaceutically acceptable salt or solvate thereof, and at least one pharmaceutically acceptable excipient.

The term "pharmaceutically acceptable excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similar. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005.

The excipients and auxiliary substances necessary to manufacture the desired pharmaceutical form of administration of the pharmaceutical composition of the invention will depend, among other factors, on the elected administration pharmaceutical form. Said pharmaceutical forms of administration of the pharmaceutical composition will be manufactured according to conventional methods known by the skilled person in the art. A review of different active ingredient administration methods, excipients to be used and processes for producing them can be found in "Tratado de Farmacia Galénica", C. Faulí i Trillo, Luzán 5, S. A. de Ediciones, 1993.

Examples of pharmaceutical compositions include any solid (tablets, pills, capsules, granules etc.) or liquid (solutions, suspensions or emulsions) compositions for oral, topical or parenteral administration.

In a preferred embodiment the pharmaceutical compositions are in oral form. Suitable dose forms for oral administration may be tablets and capsules and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically acceptable wetting agents such as sodium lauryl sulfate.

The solid oral compositions may be prepared by conventional methods of blending, filling or tabletting. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

The compounds or compositions of the present invention may be administered by any suitable method, such as oral, sublingual, intranasal, intraocular, parenteral, subcutaneous, intramuscular, intravenous, or transdermal administration. Oral administration is preferred.

Generally an effective administered amount of a compound of the invention will depend on the relative efficacy of the compound chosen, the severity of the disorder being treated and/or prevented and the weight of the sufferer. However, active compounds will typically be administered once or more times a day, for example 1, 2, 3 or 4 times daily, with typical total daily doses in the range of from 0.01 to 1000 mg/kg/day.

Synthesis of Compounds of Formula (I)

The compounds of formula (I) of the present invention can be synthesized in a multi-step sequence by available synthetic procedures. For example, they can be prepared by the process summarized in the general Scheme 1 shown below.

Scheme 1

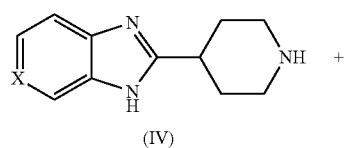

(IV)

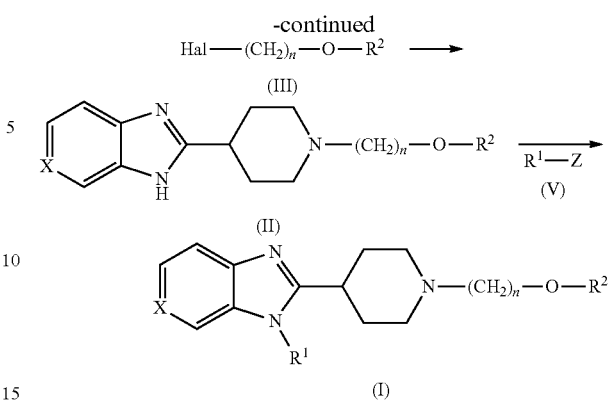

Compounds of formula (I) can be prepared by N-alkylation of a compound of formula (IV) with an alkylating agent of formula (III), wherein Hal is selected from Cl and Br, and n and $R^2$ are as previously defined for the compounds of formula (I), to give a compound of formula (II). This alkylation is carried out under standard conditions known in the art, such as heating in the presence of a base, for example sodium carbonate, potassium carbonate, cesium carbonate, trietilamine and the like, preferably sodium carbonate, in suitable organic solvent, for example N,N-dimethylformamide (DMF), acetonitrile (AcCN), tetrahydrofuran (THF) and the like, preferably DMF. The compound of formula (II) may be isolated from the reaction mixture by common procedures known by the skilled person, such as by extraction. This compound of formula (II) may be purified by common purification procedures known by the skilled person such as column chromatography, trituration and crystallization. Said compound of formula (II) is then subjected to a N-alkylation on the imidazole ring with an alkylating agent of formula (V), wherein $R^1$ is as previously defined for the compounds of formula (I) and Z is a suitable leaving group such as an halogen (such as bromo or chloro) or a tosyl group, preferably a tosyl group. This alkylation is also carried out under reaction conditions known in the art, such as heating in the presence of a base, for example potassium hydroxide, sodium carbonate, potassium carbonate, cesium carbonate, triethylamine and the like, preferably potassium hydroxide, in suitable organic solvent, for example N,N-dimethylformamide (DMF), acetonitrile (AcCN), tetrahydrofuran (THF) and the like, preferably DMF. The compound of formula (I) may be isolated from the reaction mixture by common procedures known by the skilled person, such as by extraction. This compound of formula (I) may be purified by common purification procedures known by the skilled person such as column chromatography, trituration and crystallization. Additionally, when $R^2$ is a $C_1$-$C_6$ alkyl substituted with a COOH group ($R_e$ is H) in the compound of formula (I), esterification thereof with the an alcohol ($C_1$-$C_6$ alkyl-OH) gives the corresponding compound of formula (I) wherein $R^2$ is a $C_1$-$C_6$ alkyl substituted with a COO—$C_1$-$C_6$ alkyl group ($R_e$ is $C_1$-$C_6$ alkyl). This esterification may be carried out under common reaction conditions such as by stirring at room temperature and in the presence of a suitable catalyst such as acetyl chloride.

The present invention is additionally explained below by means of examples. This explanation must by no means be interpreted as a limitation of the scope of the invention as it is defined in the claims.

EXAMPLES

Compounds of formula (I) according to the present invention were prepared following the general preparation strategy detailed below. The detailed preparation of some of the compounds is described hereinafter. All the reactants used are commercially available The $^1$HNMR were measured with a BRUKER Avance 300 MHz device in deuterated chloroform with tetramehylsilane (TMS) as the reference standard or deuterated dimethylsulfoxide.

Step 1: Synthesis of Intermediates A-F

Intermediate A. Synthesis of 2-(4-(1H-benzo[d]imidazol-2-yl)piperidin-1-yl)ethan-1-ol

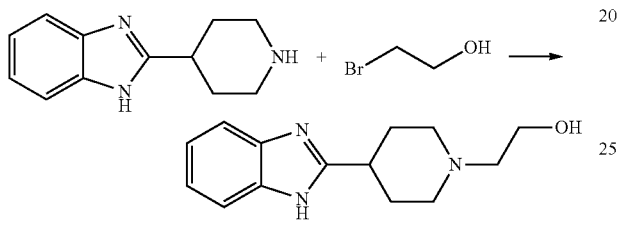

Na$_2$CO$_3$ (3.8 g, 35.8 mmol) and 2-bromoethanol (2.54 ml, 35.8 mmol) were added to a solution of 2-(piperidin-4-yl)-1H-benzo[d]imidazole (6 g, 30 mmol) in 20 ml of DMF. The reaction was heated to 100° C. under stirring for 20-24 h. Water (10 ml) was added and the mixture was extracted with CH$_2$Cl$_2$ (3×20 ml). The organic layers were dried over anhydrous sodium sulphate and the solvent was evaporated. The solid residue was triturated in diethylether to give, after filtration, 3.5 g (48% yield) of 4-(1H-benzo[d]imidazol-2-yl)piperidin-1-yl)ethan-1-ol as a yellow solid. $^1$H-NMR (DMSO): 12.1 (s, 1H) 7.5-7.4 (2d, 2H), 7.1 (m, 2H), 4.4 (m, 0.7H), 3.5 (m, 2H), 2.9 (m, 2H), 2.8 (m, 1H), 2.5 (t, 2H), 2.1-1.8 (m, 6H) ppm.

The following intermediates B-D and F were obtained following the general synthetic process described above, in particular by reaction of 2-(piperidin-4-yl)-1H-benzo[d]imidazole (intermediates B-D) or 2-piperidin-4-yl-3H-imidazol[4,5-c]pyridine (intermediate F) with the corresponding halogenated compounds (III). The obtained intermediates B-E may be purified by flash column chromatography (dichloromethane (DCM)/methanol 9:1).

Intermediate B. 3-(4-(1H-benzo[d]imidazol-2-yl)piperidin-1-yl)propan-1-ol

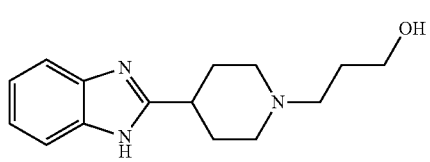 [SMILES: OCCCN1CCC(c2nc3ccccc3[nH]2)CC1]

$^1$H-NMR (DMSO) 7.4 (m, 2H), 7.1 (m, 2H), 3.4 (m, 8H), 2.9 (d, 2H), 2.8 (m, 1H) 2.3 (m, 2H), 2.0 (m, 4H), 1.9 (m, 2H), 1.6 (m, 2H) ppm.

Intermediate C. 2-(1-(2-methoxyethyl)piperidin-4-yl)-1H-benzo[d]imidazole

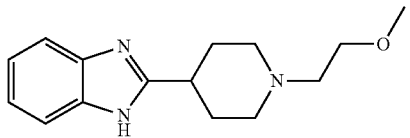 [SMILES: COCCN1CCC(c2nc3ccccc3[nH]2)CC1]

$^1$H-NMR (DMSO) 12.1 (s, 1NH), 7.4 (d, 2H), 7.1 (d, 2H), 3.5 (t, 2H), 3.2 (s, 3H), 2.9 (m, 2H), 2.8 (m, 1H), 2.5 (m, 3H), 2.1-1.8 (m, 6H) ppm.

Intermediate D. 2-(2-(4-(1H-benzo[d]imidazol-2-yl)piperidin-1-yl)ethoxy)acetic acid

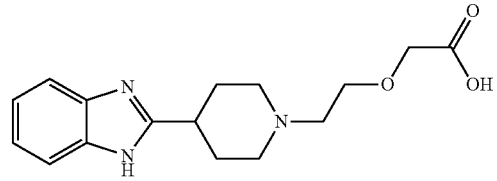 [SMILES: O=C(O)COCCN1CCC(c2nc3ccccc3[nH]2)CC1]

$^1$H-NMR (DMSO) 12.1 (s, 1H), 7.4 (m, 2H), 7.1 (m, 2H), 4.7 (s, 1H), 4.3 (d, 2H), 4.2 (d, 2H), 3.9 (d, 1H), 3.2 (m, 3H), 3.1 (m, 2H), 2.8 (m, 1H), 2.4 (m, 6H), 1.8 (m, 2H) ppm.

Intermediate E. Methyl 2-(2-(4-(1H-benzo[d]imidazol-2-yl)piperidin-1-yl)ethoxy) acetate

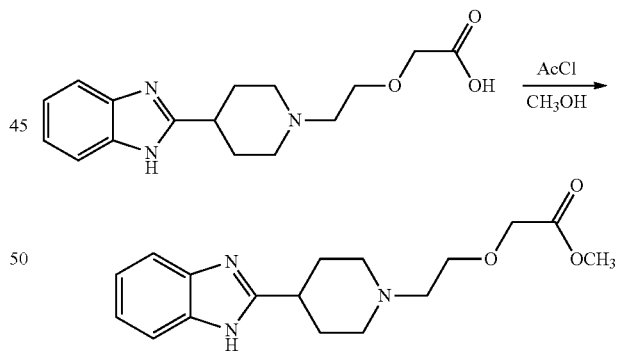

Acetyl chloride (0.1 ml, 1.44 mmol) was added to solution of 2-(2-(4-(1H-benzo[d]imidazol-2-yl)piperidin-1-yl)ethoxy)acetic acid (Intermediate D, 2 g, 7 mmol) in 15 mL of methanol. The reaction mixture was stirred for 18-20 h at room temperature. Water (10 mL) was added and the mixture was extracted with CHCl$_3$ (2×10 mL). The organic layers were dried over anhydrous sodium sulphate and the solvent was evaporated. The residue was purified with flash column chromatography (DCM/MeOH). 1.2 g (60% yield) of a yellow solid was obtained. $^1$H-NMR (CDCl$_3$) 7.6 (m, 2H), 7.2 (m, 2H), 4.1 (s, 2H), 3.8 (s+t, 5H), 3.2 (m, 2H), 3 (m, 1H), 2.75 (t, 2H), 2.4-1.8 (m, 6H) ppm.

Intermediate F. 2-[4-(3H-Imidazo[4,5-c]pyridin-2-yl)-piperidin-1-yl]-ethanol

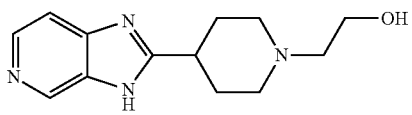

This intermediate was obtained following the general synthetic process described above in particular by reaction of 2-piperidin-4-yl-3H-imidazol[4,5-c]pyridine with 2-bromoethanol. $^1$H-NMR (DMSO) 12.1 (s, 1NH), 8.5 (m, 2H), 7.5 (d, 1H), 3.5 (m, 2H), 2.7 (m, 1H), 2.6 (m, 2H), 2.2 (m, 4H), 2.1-1.8 (m, 4H) ppm.

Step 2: Synthesis of Examples 1-11

Example 1. Synthesis of 2-(4-(1-(2-ethoxyethyl)-1H-benzo[d]imidazol-2-yl)piperidin-1-yl)ethan-1-ol

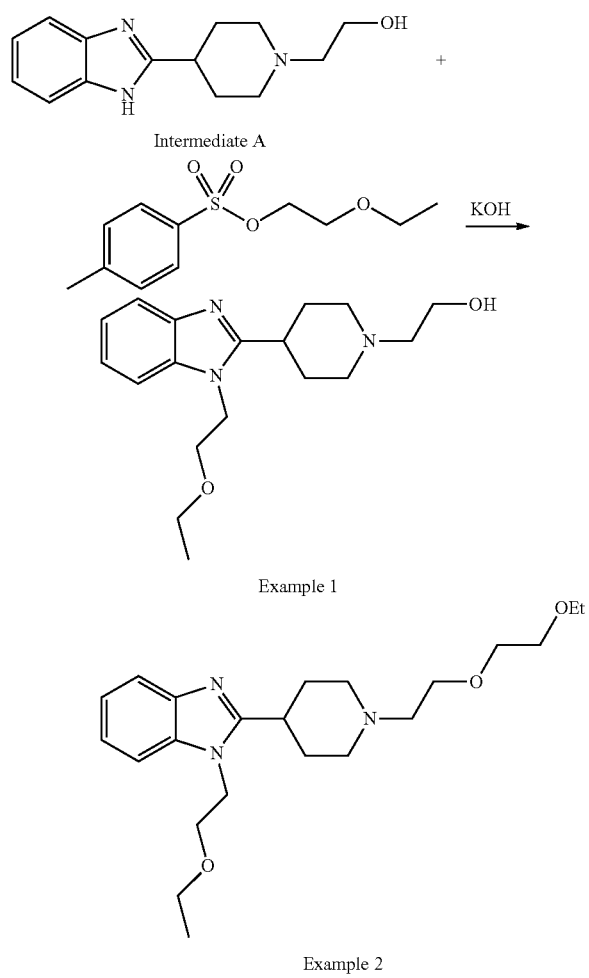

2-Ethoxyethyl 4-methylbenzenesulfonate (2.4 g, 9.7 mmol) and KOH (0.71 g, 13 mmol) were added to a solution of 2-(4-(1H-benzo[d]imidazol-2-yl)piperidin-1-yl)ethan-1-ol (Intermediate A, 1.6 g, 5.1 mmol) in 10 ml of DMF. The reaction was heated to 40-45° C.° under stirring for 5-6 h. Water (15 ml) was added and the mixture was extracted with CH$_2$Cl$_2$ (3×10 ml). The organic layers were dried over anhydrous sodium sulphate and the solvent was evaporated under vacuum to give an oil which was purified by flash chromatography (DCM/CH$_3$OH 95:5) to give 1 g (61.9% yield) of 2-(4-(1-(2-ethoxyethyl)-1H-benzo[d]imidazol-2-yl)piperidin-1-yl)ethan-1-ol as a yellow oil. $^1$H-NMR (CDCl$_3$) 7.7 (m, 1H), 7.3-7.2 (m, 3H), 4.3 (t, 2H), 3.7 (m, 4H), 3.4 (c, 2H), 3.3-3.1 (m, 4H), 2.7 (m, 2H), 2.5 (m, 2H), 2.3-2.1 (m, 4H), 1.1 (t, 3H) ppm.

Example 2. 2-(1-(2-(2-ethoxyethoxy)ethyl)piperidin-4-yl)-1-(2-ethoxyethyl)-1H-benzo [d]imidazole In the same experiment as described above as Example 1, the compound of Example 2 was also obtained 0.3 g (15% yield) as a yellow oil. $^1$H-NMR (CDCl$_3$) 7.7 (m, 1H), 7.3-7.2 (m, 3H), 4.3 (t, 2H), 3.7 (m, 4H), 3.4 (c, 2H), 3.3-3.1 (m, 4H), 2.7 (m, 2H), 2.5 (m, 2H), 2.3-2.1 (m, 4H), 1.1 (t, 3H) ppm.

The following compounds of Examples 3-4, 6-7 and 11 were obtained following the synthetic process described above for Example 1, concretely by reaction of 2-ethoxyethyl-4-methylbenzenesulfonate (examples 3, 4, 6 and 11) or 2-chloromethylpiridine (example 7), with the corresponding intermediate A-D or F.

Example 3. 3-(4-(1-(2-ethoxyethyl)-1H-benzo[d]imidazol-2-yl)piperidin-1-yl)propan-1-ol. from Intermediate B and 2-ethoxyethyl 4-methylbenzenesulfonate

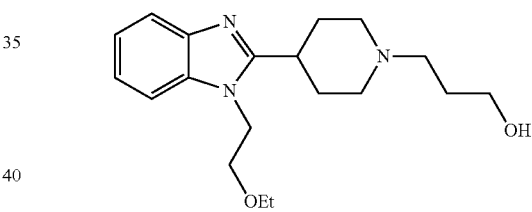

$^1$H-NMR (CDCl$_3$): 7.7 (m, 1H), 7.3-7.2 (m, 3H), 4.3 (t, 2H), 3.8 (t, 2H), 3.7 (t, 2H), 3.9 (s, 1H), 3.4 (q, 2H), 3.3 (m, 2H), 3.0 (m, 1H), 2.7 (m, 2H), 2.2 (m, 4H), 2.0 (m, 2H), 1.8 (m, 2H), 1.1 (t, 3H) ppm.

Example 4. 1-(2-ethoxyethyl)-2-(1-(2-methoxyethyl)piperidin-4-yl)-1H-benzo[d]imidazole. From intermediate C and 2-ethoxyethyl 4-methylbenzenesulfonate

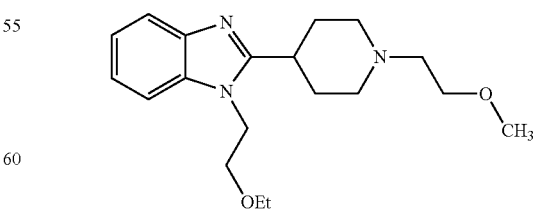

$^1$H-NMR (CDCl3): 7.7 (m, 1H), 7.3-7.2 (2m, 3H), 4.3 (m, 2H), 3.7 (t, 2H), 3.4 (t, 2H), 3.3 (s+m, 5H), 3.1 (m, 2H), 2.9 (m, 1H), 2.6 (m, 2H), 2.2 (m, 4H), 1.9 (m, 2H), 1.1 (t, 3H) ppm.

Example 5. 2-(4-(1-(2-ethoxyethyl)-1H-benzo[d]imidazol-2-yl)piperidin-1-yl)ethyl acetate from Compound of Example 1

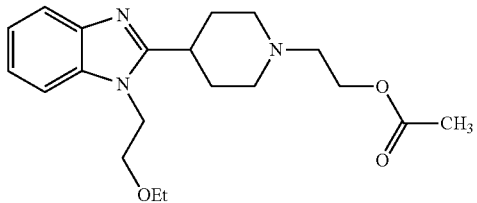 [SMILES: CCOCCn1c(C2CCN(CCOC(C)=O)CC2)nc2ccccc21]

2-(4-(1-(2-Ethoxyethyl)-1H-benzo[d]imidazol-2-yl)piperidin-1-yl)ethan-1-ol (Example 1, 0.5 g, 1.6 mmol) was dissolved in THF (4 ml) and, while keeping the reaction vessel in an ice bath, triethylamine (TEA) (0.2 ml) and acetyl chloride (0.112 ml, 1.6 mmol) were added. Then the reaction mixture was left to reach room temperature and further stirred for approximately 20 h. Then, water was added and the mixture was extracted with diethyl ether (2×20 mL), dried over anhydrous sodium sulphate and concentrated to give 0.4 g of a yellowish oil which was purified by column flash chromatography (DCM/CH$_3$OH 9:1) to give 0.28 g of an oil which solidifies over diethyl ether/heptane. The solid was filtered and washed with heptane to give 0.16 g (25% yield) of the title compound as a solid. $^1$H-NMR (CDCl$_3$): 7.7 (m, 1H), 7.3-7.12 (m, 3H), 4.3 (m, 4H), 3.7 (t, 2H), 3.4 (c, 2H), 3.3-4 (m, 3H), 2.8 (m, 2H), 2.4-1.9 (m+s, 10H), 1.1 (t, 3H) ppm.

Example 6. 2-(2-(4-(1-(2-ethoxyethyl)-1H-benzo[d]imidazol-2-yl)piperidin-1-yl) ethoxy)acetic acid. From Intermediate D and 2-ethoxyethyl 4-methyl-benzenesulfonate

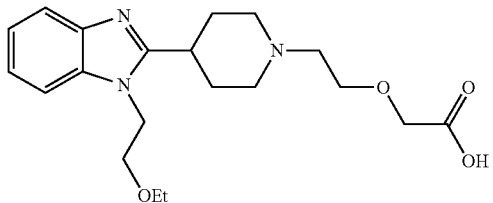 [SMILES: CCOCCn1c(C2CCN(CCOCC(=O)O)CC2)nc2ccccc21]

$^1$H-NMR (CDCl$_3$): 7.8 (m, 1H), 7.3 (m, 3H), 4.7 (d, 1.2H), 4.4-4.2 (t+q, 5H), 4.0 (d, 1.4H), 3.7 (m, 7H), 3.4 (m, 3H), 3.2 (t, 1H), 2.8 (m, 1.5H), 2.0 (m, 3H), 1.1 (t, 3H) ppm.

Example 7. 2-(4-(1-(pyridin-2-ylmethyl)-1H-benzo[d]imidazol-2-yl)piperidin-1-yl)ethan-1-ol. From Intermediate A and 2-(chloromethyl)pyridine

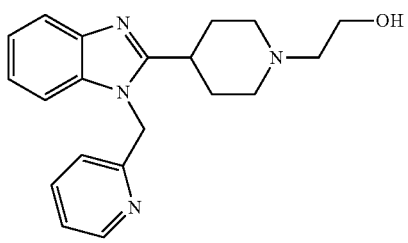 [SMILES: OCCN1CCC(c2nc3ccccc3n2Cc2ccccn2)CC1]

$^1$H-NMR (CDCl$_3$): 8.5 (d, 1H), 7.8 (m, 1H), 7.6 (t, 1H), 7.2 (m, 4H), 6.8 (d, 1H), 5.4 (s, 2H), 3.8 (m, 3H), 3.5-3.2 (m, 1H), 2.9 (m, 4H), 2.2 (m, 4H) ppm.

Example 8. Ethyl 2-(2-(4-(1-(2-ethoxyethyl)-1H-benzo[d]imidazol-2-yl)piperidin-1-yl)ethoxy)acetate

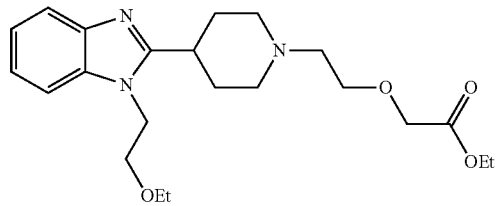 [SMILES: CCOCCn1c(C2CCN(CCOCC(=O)OCC)CC2)nc2ccccc21]

This compound was obtained following the synthetic process described above for Intermediate E but by esterification of the compound obtained in Example 6 with ethanol and acetyl chloride as catalyser. $^1$H-NMR (CDCl$_3$): 7.5 (m, 1H), 7.2 (m, 3H), 4.3 (m, 6H), 3.7 (m, 4H), 3.4 (q, 2H), 3.2 (m, 2H), 3.1 (m, 1H), 2.7 (m, 2H), 2.4 (m, 2H), 2.2 (m, 2H), 2.0 (m, 2H), 1.3 (t, 3H), 1.1 (t, 3H) ppm.

Example 9. Methyl 2-(2-(4-(1-(2-phenoxyethyl)-1H-benzo[d]imidazol-2-yl)piperidin-1-yl)ethoxy) acetate

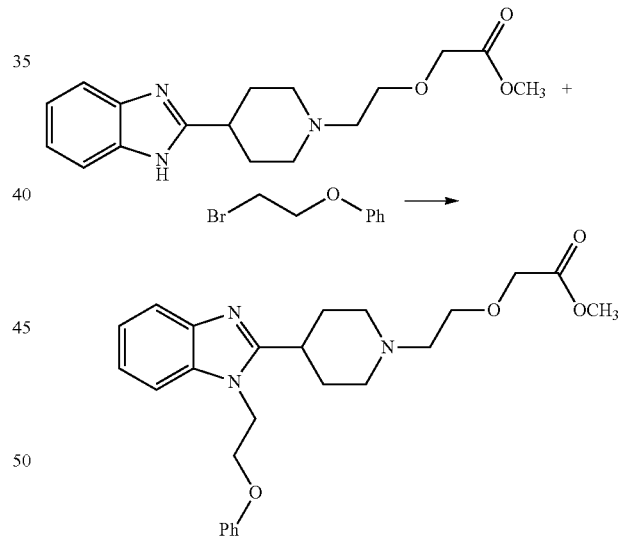

2-(Bromoethoxy)benzene (0.8 g, 0.6 ml, 3.9 mmol) and KOH (0.21 g, 3.9 mmol) were added to a solution of methyl 2-(2-(4-(1H-benzo[d]imidazol-2-yl)piperidin-1-yl)ethoxy) acetate (Intermediate E, 1.1 g, 2.6 mmol) in 15 ml of DMF. The reaction was heated to 40-45° C. under stirring for 5-6 h. Water (5 ml) was added and the mixture was extracted with CH$_2$Cl$_2$ (2×20 ml). The organic layers were dried over anhydrous sodium sulphate and the solvent was evaporated under vacuum to give an oil which was purified by flash chromatography (DCM/CH$_3$OH 90:10) to give 0.6 g (48.5% yield) of methyl 2-(2-(4-(1-(2-phenoxyethyl)-1H-benzo[d] imidazol-2-yl)piperidin-1-yl)ethoxy) acetate as a solid. $^1$H-NMR (CDCl$_3$): 7.7 (m, 1H), 7.4-7.1 (m, 6H), 7.0 (m, 1H), 6.8 (d, 2H), 4.6 (m, 2H), 4.3 (m, 2H), 4.1 (s, 2H), 3.8-3.7 (s+t, 5H), 3.3-3.0 (m, 3-4H), 2.7 (m, 2H), 2.3 (m, 4H), 2.0 (m, 2H) ppm.

Example 10. 2-(2-(4-(1-(2-phenoxyethyl)-1H-benzo[d]imidazol-2-yl)piperidin-1-yl) ethoxy)acetic acid

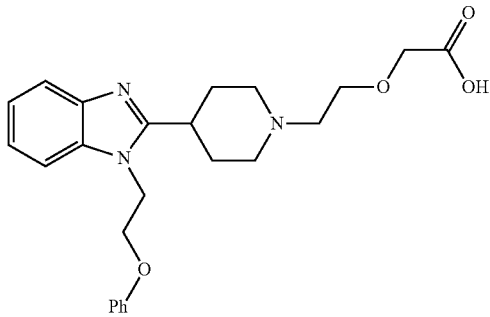 [SMILES: O=C(O)COCCN1CCC(c2nc3ccccc3n2CCOc2ccccc2)CC1]

The following compound was prepared in analogous way as described above for Example 9, but starting from intermediate D. ¹H-NMR (CDCl₃): 7.7 (d, 1H), 7.4 (d, 1H), 7.2 (m, 4H), 6.9 (t, 1H), 6.7 (d, 2H), 4.7 (d, 1H), 4.5 (m, 2H), 4.2 (m, 5H), 3.9 (d, 1H), 3.7 (d, 4H), 3.3 (m, 1H), 3.1 (t, 1H), 2.7 (m, 1H), 2.1-1.9 (m, 4H) ppm.

Example 11. 2-{4-[3-(2-Ethoxy-ethyl)-3H-imidazo[4,5-c]pyridin-2-yl]-piperidin-1-yl}-ethanol. this Compound was Prepared from Intermediate F and ethoxyethyl 4-methylbenzenesulfonate

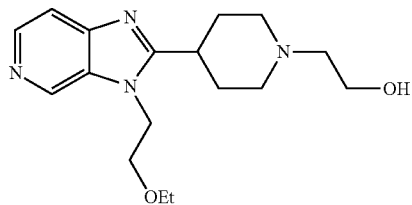 [SMILES: CCOCCn1c(C2CCN(CCO)CC2)nc2ccncc21]

¹H-NMR (CDCl₃): 8.84 (d, 1H), 8.32 (d, 1H), 7.66 (dd, 1H), 4.55 (t, 2H), 3.84-3.75 (m, 4H), 3.45-3.31 (m, 5H), 2.85 (t, 2H), 2.61 (t, 2H), 2.25-2.05 (m, 4H), 1.05 (t, 3H) ppm.

Example 12. 2-(4-(3-(2-phenoxyethyl)-3H-imidazo[4,5-c]pyridin-2-yl)piperidin-1-yl)ethan-1-ol. this Compound was Prepared from Intermediate F and 2-phenoxyethyl bromide

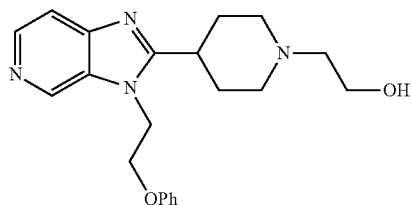

¹H-NMR (CDCl₃): 8.85 (d, 1H), 8.33 (d, 1H), 7.72 (dd, 1H), 7.20 (t, 2H), 6.88 (t, 1H), 6.74 (d, 2H), 4.74 (t, 2H), 4.36 (t, 2H), 3.75 (t, 2H), 3.14-3.31 (m, 3H), 2.66 (t, 2H), 2.34 (dt, 2H), 2.20-1.97 (m, 4H) ppm.

Example 13. 2-(4-(3-(pyridin-2-ylmethyl)-3H-imidazo[4,5-c]pyridin-2-yl)piperidin-1-yl)ethan-1-ol. this Compound was Prepared from Intermediate F and 2-chloromethylpyridine

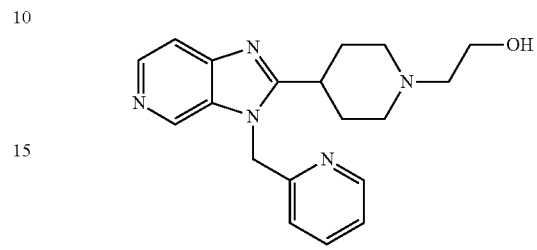

¹H-NMR (CD₃OD): 8.73 (s, 1H), 8.50 (d, 1H), 8.48 (dd, 1H), 7.83 (t, 1H), 7.66 (dd, 1H), 7.31-7.35 (m, 2H), 5.75 (s, 2H), 3.71 (t, 2H), 3.34-3.08 (m, 3H), 2.59 (t, 2H), 2.29-2.20 (m, 2H), 2.17-2.03 (m, 2H), 1.93-1.88 (m, 2H) ppm.

BIOLOGICAL ASSAYS

Affinity for histamine H1-receptor was determined by binding studies to H1 receptors. The sample used is a suspension of membranes of CHO cells transfected with the human H1 receptor (5 mg/ml, PerkinElmer), stored at −80° C. until use. After thawing, the membranes were homogenized in assay buffer (50 mM Na/K phosphate) prepared in purified water and kept at room temperature (pH 7.4). The assay was performed in 96-well microplates. In each well, 25 µl of buffer and 25 µl of vehicle (total binding) or 10 µM pyrilamine (nonspecific binding) or the products to be tested was added. Subsequently, 200 µl of the membrane suspension was added to all wells and the microtiter plate was preincubated at 25° C. for 15 min. After this time, 25 µl of 3H-pyrilamine (1.5 nM) was added and the reaction was allowed to incubate for 60 min at 25° C. Then, free radioligand was quickly separated from bound radioligand by vacuum filtration (Multiscreen microplate Screener), performing 10 washes with assay buffer (4° C.). Subsequently 45 µl of scintillation fluid was added to each well and after sealing of the microplate, the radioactivity was quantified in a liquid scintillation counter (TopCount). The graphs of the inhibition curves and calculation the IC50 value were generated with the GraphPad Prism program. The IC50 values are provided in Table 1.

TABLE 1

Affinity for human histamine $H_1$-receptor

| Compound | n | $IC_{50}$ (nM) |
|---|---|---|
| Example 1 | 2 | 25 |

TABLE 1-continued

Affinity for human histamine H$_1$-receptor

| Compound | n | IC$_{50}$ (nM) |
|---|---|---|
| 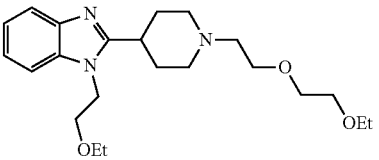 Example 2 | 2 | 115 |
| 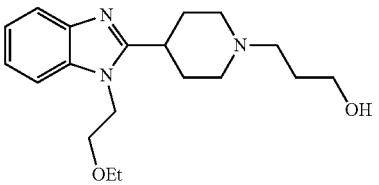 Example 3 | 2 | 28 |
| 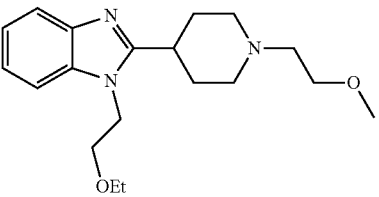 Example 4 | 2 | 93 |
| 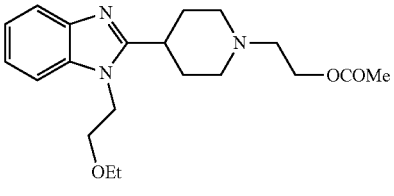 Example 5 | 2 | 54 |
| 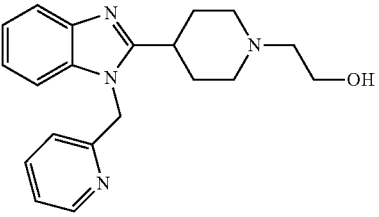 Example 7 | 2 | 175 |
| 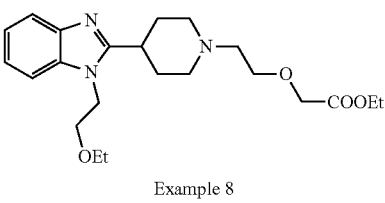 [SMILES: CCOCCn1c(C2CCN(CCOCC(=O)OCC)CC2)nc2ccccc21] Example 8 | 2 | 169 |

TABLE 1-continued

Affinity for human histamine H$_1$-receptor

| Compound | n | IC$_{50}$ (nM) |
|---|---|---|
| 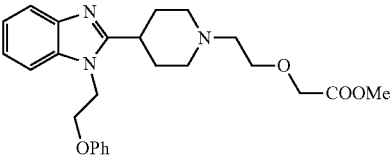 Example 9 | 2 | 195 |

Affinity for histamine H$_1$-receptor of four compounds from the state of the art was determined by binding studies to H$_1$ receptors using the same protocol as described above. The graphs of the inhibition curves and calculation the IC$_{50}$ value were generated also with the GraphPad Prism program. The IC$_{50}$ values are provided in Table 2.

TABLE 2

Affinity for human histamine H$_1$-receptor for comparative compounds

| Compound | IC$_{50}$ (nM) |
|---|---|
| 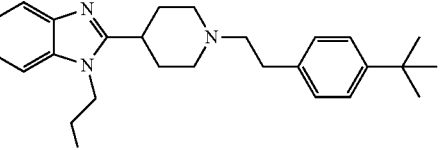 Example 5 in EP 0580541 | 424 |
| 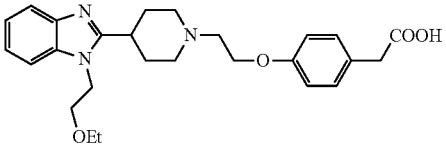 Compound I-8 in CN 103896915 | 1990 |
| 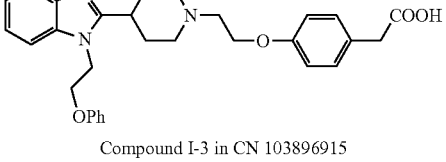 Compound I-3 in CN 103896915 | 271 |
| 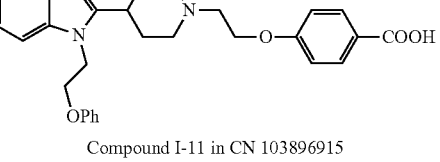 Compound I-11 in CN 103896915 | 260 |

As shown above, the compounds of formula (I) of the invention provide an improved affinity for human histamine H$_1$-receptor over compounds of the state of the art lacking an oxygen atom in the alkylene chain (Examples 1-5 and 8 of the invention v. Example 5 in EP 0580541) and over compounds having an aryloxy group in the alkylene chain (Examples 1-5 and 8 of the invention v. Compound I-8 in CN 103896915 and Example 9 of the invention v. Compounds I-3 and I-11 in CN 103896915).

Antihistaminic activity: histamine papules [Mota I., *Life Sci.*, 1963, 12, 917-927; Lefebvre P. et al., *C. R. Soc. Biol.*, 1962, 156, 183-186; and Udaka K. et al., *Proc Soc Exp Biol Med*, 1970, 133, 1384-1387]

Rats, males and/or females (110-160 g) were used, kept under the usual conditions of temperature and humidity. Previous day, backs of the animals were shaved and since that time (16-24 h) animals were subjected to solid fast but supplied ad libitum with an aqueous solution of sucrose (8%) and sodium chloride (0.2%). The compounds to be tested were dissolved in tartaric acid (Probus 015420) 0.1 M at a concentration of 5 mg/ml and then diluted with water until the concentration to be tested. This suspension or solution of the compound to be tested was administered by rigid oral gavage at 10 mL/kg. The control group received by the same administration mode a solution of tartaric acid (Probus 015420) 0.1 M in water. One hour after oral administration (products, patterns or vehicle), and under light ether anesthesia, two bumps were made on the shaved back by intradermal injection of Histamine hydrochloride (Sigma H-7250) dissolved in sterile saline (10 mg/0.1 mL/papule). Immediately after, dye injection of Evans blue (Merck No. 3169) dissolved in sterile saline (25 mg/kg/4 mL) was administered intravenously. Thirty minutes after intravenous dye injection, the animals are sacrificed under a $CO_2$ atmosphere, dorsal skin was extracted and freezed to facilitate cutting; subsequently, spots were cut, Evans Blue dye punched and extracted (48 h; 50° C.) with 5 mL of formamide (Merck No. 9684). The concentration of extracted Evans blue was determined by microplate reader.

TABLE 3

| Compound | Dose (mg/kg) | n | % inhibition |
|---|---|---|---|
| 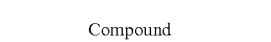 | 20 | 6 | 45.03 |

The invention claimed is:
1. A compound of formula (I):

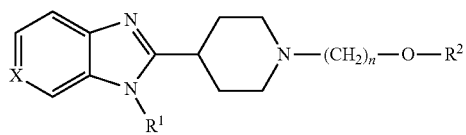

wherein:
$R^1$ is an optionally substituted $C_1$-$C_6$ alkyl group;
$R^2$ is selected from hydrogen, —$COR_b$, —$COOR_c$ and $C_1$-$C_6$ alkyl optionally substituted with —$OR_d$, or —$COOR_e$, wherein $R_b$, $R_c$, $R_d$ and $R_e$ are independently selected from hydrogen and $C_1$-$C_6$ alkyl;
n is 1, 2 or 3;
X is CH or N;
or a pharmaceutically acceptable salt or solvate thereof.
2. The compound according to claim 1, wherein X is CH.
3. The compound according to claim 1, wherein $R^1$ is a $C_1$-$C_6$ alkyl group optionally substituted with $C_1$-$C_6$ alkyl, $C_3$-$C_7$ cycloalkyl, 3- to 10-membered heterocyclyl, $C_6$-$C_{12}$ aryl, 3- to 10-membered heteroaryl, halogen, CN, $NO_2$, $NH_2$, $NH(C_1$-$C_6$ alkyl), $N(C_1$-$C_6$ alkyl)$_2$, or —$OR_a$, wherein $R_a$ is selected from hydrogen, $C_1$-$C_6$ alkyl, halo($C_1$-$C_6$ alkyl), $C_3$-$C_7$ cycloalkyl, 3- to 10-membered heterocyclyl, $C_6$-$C_{12}$ aryl, ($C_6$-$C_{12}$)aryl($C_1$-$C_6$)alkyl, and 3- to 10-membered heteroaryl.
4. The compound according to claim 1, wherein $R^1$ is a $C_1$-$C_6$ alkyl group optionally substituted with 3- to 10-membered heteroaryl or —$OR_a$, wherein $R_a$ is selected from hydrogen, $C_1$-$C_6$ alkyl, $C_6$-$C_{12}$ aryl, ($C_6$-$C_{12}$)aryl($C_1$-$C_6$)alkyl, and 3- to 10-membered heteroaryl.
5. The compound according to claim 1, wherein $R^1$ is a $C_1$-$C_6$ alkyl group optionally substituted with 5- to 6-membered heteroaryl or —$OR_a$, wherein $R_a$ is selected from $C_1$-$C_6$ alkyl, phenyl, and 5- to 6-membered heteroaryl.
6. The compound according to claim 1, wherein $R^1$ is a $C_1$-$C_6$ alkyl group substituted with —$OC_1$-$C_6$ alkyl.
7. The compound according to claim 1 which is selected from the following compounds:

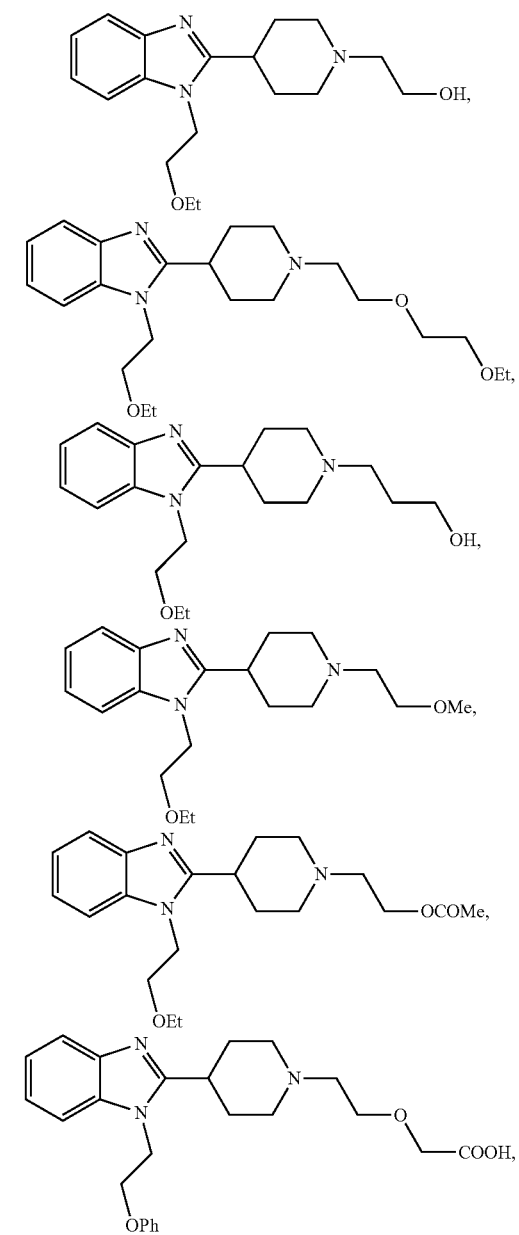

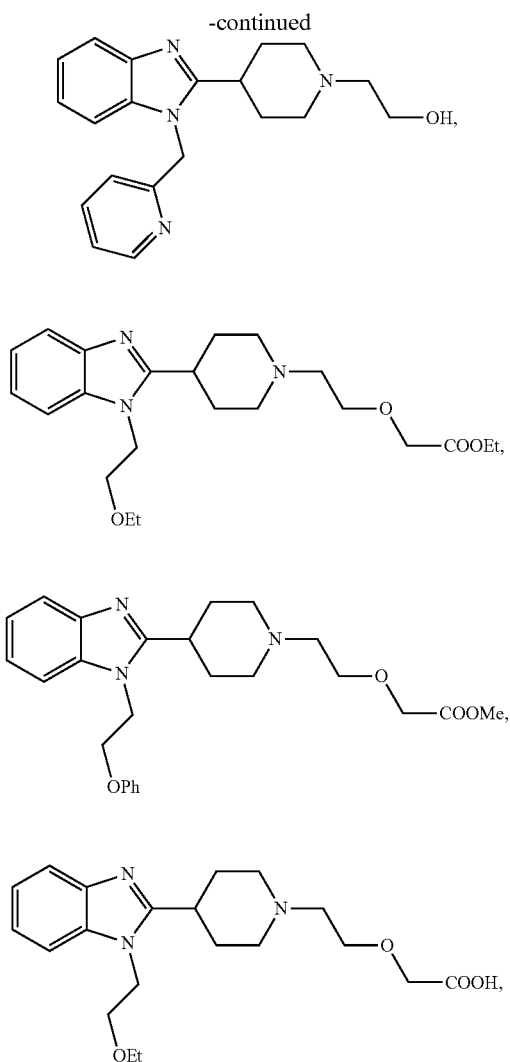

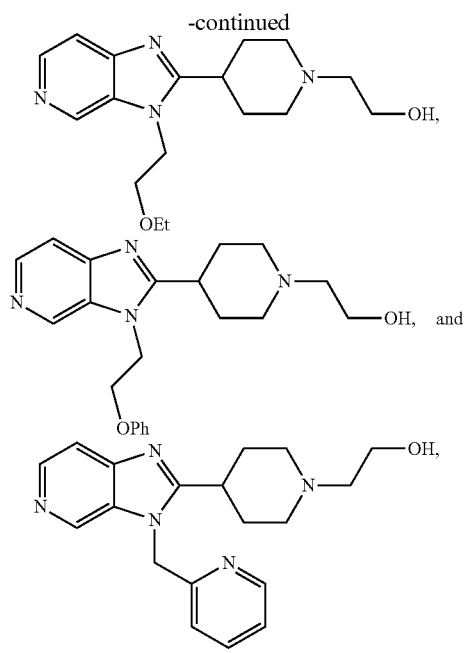

or a pharmaceutically acceptable salt or solvate thereof.

8. A pharmaceutical composition comprising a compound of formula (I) as defined in claim 1 or a pharmaceutically acceptable salt or solvate thereof, and at least one pharmaceutically acceptable excipient.

9. A method of treatment of an allergic disorder or disease, which method comprises administering to a patient in need of such a treatment a therapeutically effective amount of a compound of formula (I) as defined in claim 1 or a pharmaceutically acceptable salt or solvate thereof, wherein the allergic disorder or disease is selected from rhinitis, conjunctivitis, rhinoconjunctivitis, dermatitis, urticaria and asthma.

* * * * *